(12) United States Patent
Guger et al.

(10) Patent No.: US 11,191,475 B2
(45) Date of Patent: Dec. 7, 2021

(54) METHOD FOR DETERMINING THE PERCEPTIVENESS OF A SUBJECT

(71) Applicants: Christoph Guger, Piberbach (AT); Guenter Edlinger, Graz (AT)

(72) Inventors: Christoph Guger, Piberbach (AT); Guenter Edlinger, Graz (AT)

(*) Notice: Subject to any disclaimer, the term of this patent is extended or adjusted under 35 U.S.C. 154(b) by 932 days.

(21) Appl. No.: 15/510,337

(22) PCT Filed: Apr. 29, 2016

(86) PCT No.: PCT/AT2016/050117
§ 371 (c)(1),
(2) Date: May 3, 2017

(87) PCT Pub. No.: WO2017/185109
PCT Pub. Date: Nov. 2, 2017

(65) Prior Publication Data
US 2018/0092566 A1    Apr. 5, 2018

(51) Int. Cl.
*A61B 5/377*    (2021.01)
*A61B 5/16*    (2006.01)
*A61B 5/00*    (2006.01)

(52) U.S. Cl.
CPC ........ *A61B 5/377* (2021.01); *A61B 5/16* (2013.01); *A61B 5/4064* (2013.01); *A61B 5/7267* (2013.01); *A61B 2505/03* (2013.01)

(58) Field of Classification Search
None
See application file for complete search history.

(56) References Cited

U.S. PATENT DOCUMENTS

| 6,092,058 A * | 7/2000 | Smyth ............... A61B 5/04842 600/554 |
| 2004/0162489 A1* | 8/2004 | Richards-Kortum ...... A61B 5/0071 600/473 |

(Continued)

FOREIGN PATENT DOCUMENTS

| JP | 2015530895 A | 10/2015 |
| JP | 2015533559 A | 11/2015 |

(Continued)

OTHER PUBLICATIONS

King, Jr. et al., "Single-trial decoding of auditory novelty responses facilitates the detection of residual consciousness", Dec. 1, 2013, pp. 726-738.

(Continued)

*Primary Examiner* — Matthew Kremer
(74) *Attorney, Agent, or Firm* — Laurence A. Greenberg; Werner H. Stemer; Ralph E. Locher

(57) ABSTRACT

The perceptive faculties of a subject are determined by way of a brain-computer interface 20. At least two mutually distinguishable types of stimuli $S_A$, $S_B$ which are applicable to a subject are prescribed. A multiplicity of temporally successive stimuli are applied to the subject and combined to form blocks. Calibration data are created from the EEG data ascertained thus by virtue of a number of ascertained EEG data and stimuli associated with these EEG data are combined to form calibration blocks. A classification function is ascertained by a classification analysis on the basis of ascertained calibration blocks. The classification function specifies a position of the stimulus of the first type in the respective calibration block. Finally, the EEG data of a number of test blocks selected from the blocks are subjected to the classification function.

15 Claims, 3 Drawing Sheets

(56) References Cited

U.S. PATENT DOCUMENTS

| | | | |
|---|---|---|---|
| 2014/0228701 A1* | 8/2014 | Chizeck | A61B 5/04012 600/544 |
| 2014/0347265 A1* | 11/2014 | Aimone | A61B 5/165 345/156 |
| 2015/0230744 A1 | 8/2015 | Faubert et al. | |
| 2016/0360992 A1 | 12/2016 | Guger et al. | |

FOREIGN PATENT DOCUMENTS

| | | |
|---|---|---|
| WO | 2012104853 A2 | 8/2012 |
| WO | 2014052938 A1 | 4/2014 |
| WO | 2015058223 A1 | 4/2015 |

OTHER PUBLICATIONS

Anuradha Saha et al.: "EEG Analysis for Olfactory Perceptual-Ability Measurement Using a Recurrent Neural Classifier", IEEE Transactions on Human Machine Systems, vol. 44, No. 6, Dec. 2014, pp. 717-730.

\* cited by examiner

METHOD FOR DETERMINING THE PERCEPTIVENESS OF A SUBJECT

BACKGROUND OF THE INVENTION

Field of the Invention

The invention relates to a method for determining the perception or perceptive quality of a subject, in particular of a human, by means of a brain-computer interface.

The prior art has disclosed a multiplicity of different methods for determining the perception or perceptive quality of subjects, with all these methods applying different types of stimuli to the subject and testing on the basis of the reaction of the subject in the form of brain waves as to whether or not the relevant subject exhibits an adequate mental activity on account of the stimuli.

A particular problem in the prior art is that it is often difficult to evaluate the reaction of the subject and that the perception or perceptive quality of the subject occasionally decreases or increases during the test; in particular, a problem arising in the case of comatose patients is that it is unclear whether the relevant patient or subject is currently asleep. In this context, it is possible for the subject to fall asleep after a training phase, during which they are awake, and the established test shows a very poor perception of the subject whereas, in principle, the subject is however by all means capable of perception. This leads to an incorrect assessment of the mental state and may occasionally have significant consequences for the relevant patient or subject, especially since such tests are only performed very infrequently.

BRIEF SUMMARY OF THE INVENTION

The invention removes these problems of a method as set forth at the outset by way of the features of the patent claims.

The invention comprises a method for determining the perception or perceptive quality of a subject by means of a brain-computer interface, said method comprising the following steps:

a) At least two mutually distinguishable types of stimuli which are applicable to a subject, in particular acoustic, mechanical, electric or optical stimuli, are prescribed, wherein the subject is instructed, in particular, to carry out a specific mental act, preferably to count, when a specific stimulus is present.

b) A multiplicity of temporally successive stimuli are applied to the subject, the stimuli applied to the subject are combined to form blocks, wherein the blocks comprise a number of stimuli applied to the subject temporally in succession, a stimulus of a first type being arranged at a prescribed position of the block and stimuli of one or more further types being arranged at the remaining positions of the block in each case, the reaction of the subject is assessed after each of the stimuli by virtue of the EEG data of the subject caused by the stimulus or having a temporal relationship therewith being ascertained and these EEG data being assigned to the respective stimulus and the respective block at the relevant position.

c) Calibration data are created from the EEG data ascertained thus by virtue of a number of ascertained EEG data and stimuli assigned to these EEG data being combined to form calibration blocks, wherein the EEG data of the subject upon application of a first stimulus are respectively assigned to one place and the EEG data of the subject upon application of a further stimulus are assigned to the remaining places in each individual calibration block, and wherein a classification function is ascertained by means of a classification analysis on the basis of ascertained calibration blocks, said classification function specifying the position of the stimulus of the first type in the respective calibration block on the basis of EEG data of a block of stimuli.

d) The EEG data of a number of test blocks selected from the blocks are subjected to the ascertained classification function and a classification result is ascertained. An examination is carried out as to whether the position at which the stimulus of the first type is situated in the respective test block corresponds to the classification result. The number of test blocks for which a correspondence is identified is used as a measure for the perception of a subject at the time of recording the further EEG data.

In this context, it is particularly advantageous that the time at which the individual EEG data were ascertained only plays a subordinate role within the scope of assessing the perception or perceptive quality.

A particularly advantageous variant of the invention, by means of which comprehensive mixing of the individual EEG data recorded at different times may be achieved, provides that steps c) and d) are executed multiple times on the basis of the same ascertained blocks, wherein, respectively during each individual execution of steps c) and d)

individual blocks are selected in step c) as calibration blocks, in particular according to random criteria, wherein this selection, in particular, comprises at least 50% of the blocks, of the remaining ascertained blocks, in particular all remaining blocks are subjected to the classification function as test blocks in step d), wherein a separate measure for the perception or perceptive quality is respectively ascertained every time steps c) and d) are executed, and that a further measure for the perception or perceptive quality is ascertained by averaging or aggregating the separate measures obtained in the individual executions.

An advantageous procedure which facilitates continuous adaptation of the relevant perception measure and which exhibits convergence to a certain maximum value in the case of patients with complete perceptive capability provides that blocks are continuously ascertained in accordance with step b), wherein steps c) and d) are respectively executed on the basis of the previously ascertained blocks after one or more blocks were recorded, wherein, respectively during each individual execution of steps c) and d)

individual blocks are selected in step c) as calibration blocks, in particular according to random criteria, wherein this selection, in particular, comprises at least 50% of the blocks, of the remaining ascertained blocks, in particular all remaining blocks are subjected to the classification function as test blocks in step d), wherein a separate measure for the perception or perceptive quality is respectively ascertained every time steps c) and d) are executed, and that an examination is carried out in respect of how many blocks are recorded before the separate measure for the perception or perceptive quality exceeds a prescribed threshold and the number of blocks is ascertained as a further measure for the perception or perceptive quality, and/or that the mean value or the median of the individual separate measures is ascertained as a further measure for the perception or perceptive quality.

In order to obtain an evaluation which is as complete as possible of all EEG data obtained within the scope of the recording, there may be provision for individual blocks to be selected in step c) as calibration blocks, in particular according to random criteria, wherein this selection, in particular, comprises at least 50% of the blocks, for of the remaining ascertained blocks, in particular all remaining blocks or at least 10% of the remaining blocks to be subjected to the classification function as test blocks in step d) and an examination to be carried out as to whether the position at which the stimulus of the first type is situated in the respective block corresponds to the classification result.

In order to be able to subsequently undertake the determination of the perception of the respective subject again in a simple and fast manner, provision may be made for a number of successive further stimuli to be applied to the subject after formation of the classification function, said further stimuli being combined in accordance with step b) to form further blocks, and for an individual examination to be carried out in each case for these as to whether the position at which the stimulus of the first type is situated in the respective further block corresponds to the classification result and the number of further blocks for which a correspondence is identified to be used as a measure for the perception of a subject at the time of recording the further EEG data.

An increase in the measure of the perception of the subject may additionally be achieved by virtue of at least one of the stimuli, in particular all stimuli or at least stimuli of the first type, being applied to the subject in a vibrotactile manner, and by virtue of an activation stimulus being applied to the subject if a classification result exceeding a threshold is present.

Here, in particular, provision may be made in a preferred embodiment of the invention for the activation stimulus applied to the subject to consist of an application of functional electrostimulation or an application with an orthosis, a prosthesis or a robot on a region of the body of the subject, by means of which the body of the subject is stimulated at a place or by means of which a part of the body of the subject, which was stimulated in a vibrotactile manner, is manipulated.

A further preferred embodiment of the invention, which may be carried out on a multiplicity of patients, even in patients without the faculty of sight, provides for the set of the types of stimuli to be prescribed by different sounds, in particular having different durations, frequencies and volumes, at frequencies which are audible for a human and the respective sound to be played to the subject, or for the set of the types of stimuli to comprise applications of vibrations to different body parts and/or with different intensities and/or durations, said applications of vibrations being applied to the subject by means of vibration units.

A further preferred embodiment of the invention, which may be carried out on a multiplicity of patients, even on patients without the faculty of hearing, provides for the set of the types of stimuli to comprise visual stimuli for one eye or both eyes and/or visual stimuli with different intensities and/or durations, said visual stimuli being applied to the subject by means of a screen or by means of luminous means, or for the set of the types of stimuli to comprise electrical stimuli at different body parts and/or electrical stimuli with different intensities and/or durations, said electrical stimuli being applied to the subject by means of electrical stimulators.

Particularly good identifiability in the EEG data may be achieved if, depending on the respective type of stimulus, the subject is tasked with one of the following mental acts:
  counting or calculating,
  thinking of movements of body parts, in particular extremities of the right or left body half, preferably the arms or hands.

A particularly advantageous analysis of the EEG data may be achieved by virtue of the classification analysis being carried out as follows:
  discriminant function analysis, in particular linear discriminant function analysis,
  support vector machines,
  neural networks.

For the purposes of determining the dependence of the perception and perceptive quality of the subject on external influences, provision may be made, after determining the perception or perceptive quality, for the subject to be brought into different states by cooling or heating the body or a part of the body and/or by medication or for the oxygen partial pressure to be changed in the region of the subject and the perception or perceptive quality to be repeated according to the same criteria and a new measure to be ascertained for the perception or perceptive quality and the measure and the new measure to be compared to one another.

For the same purpose, provision may advantageously be made, after formation of the classification function, for the subject to be brought into different states by cooling or heating the body or a part of the body and/or by medication or for the oxygen partial pressure to be changed in the region of the subject, and for a number of successive further stimuli to be applied to the subject, said further stimuli being combined in accordance with step b) to form further blocks, and for an individual examination to be carried out in each case for these as to whether the position at which the stimulus of the first type is situated in the respective further block corresponds to the classification result and the number of further blocks for which a correspondence is identified to be used as a new measure for the perception of a subject at the time of recording the further EEG data, and for the measure and the new measure to be compared to one another.

An advantageous feedback to the subject may be achieved by virtue of the recorded EEG data being classified by means of the previously executed classification analysis and, if an ascertained result is available from the classification, by virtue of an activation stimulus assigned to this result being applied to the subject.

In the following text, a preferred exemplary embodiment of the invention is illustrated on the basis of the figures of the drawing specified below.

DESCRIPTION OF THE INVENTION

Figure 1:
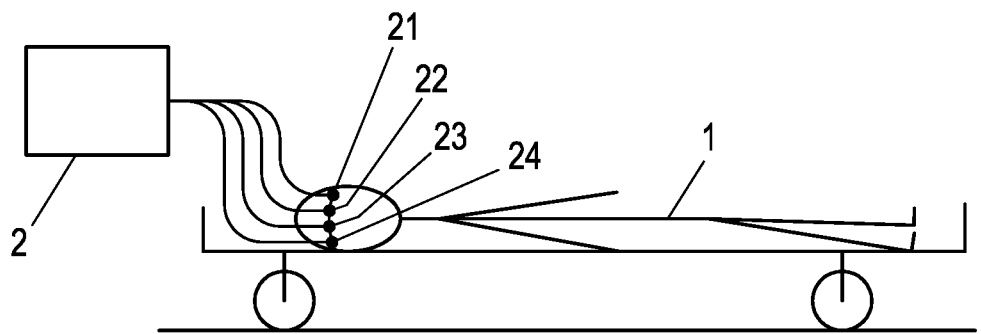
FIG. 1 depicts a subject 1 lying on a bed.
Figure 2:
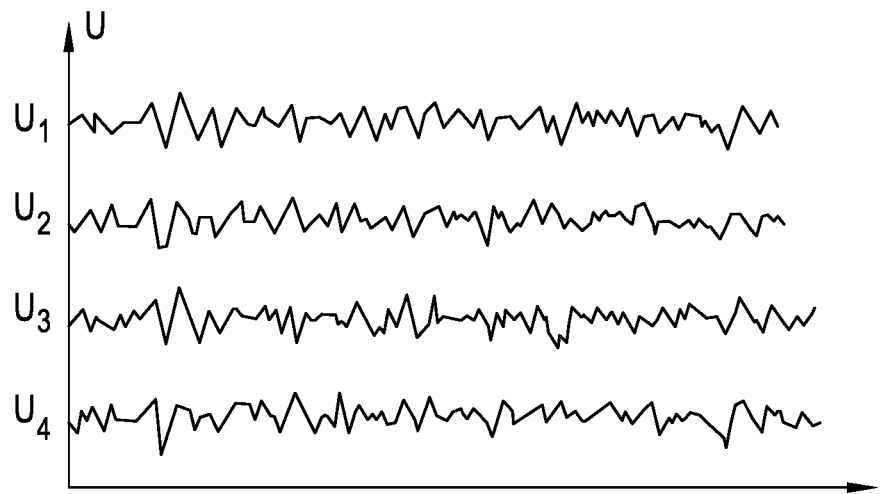
FIG. 2 shows voltage signals ascertained using EEG electrodes.
Figure 3:
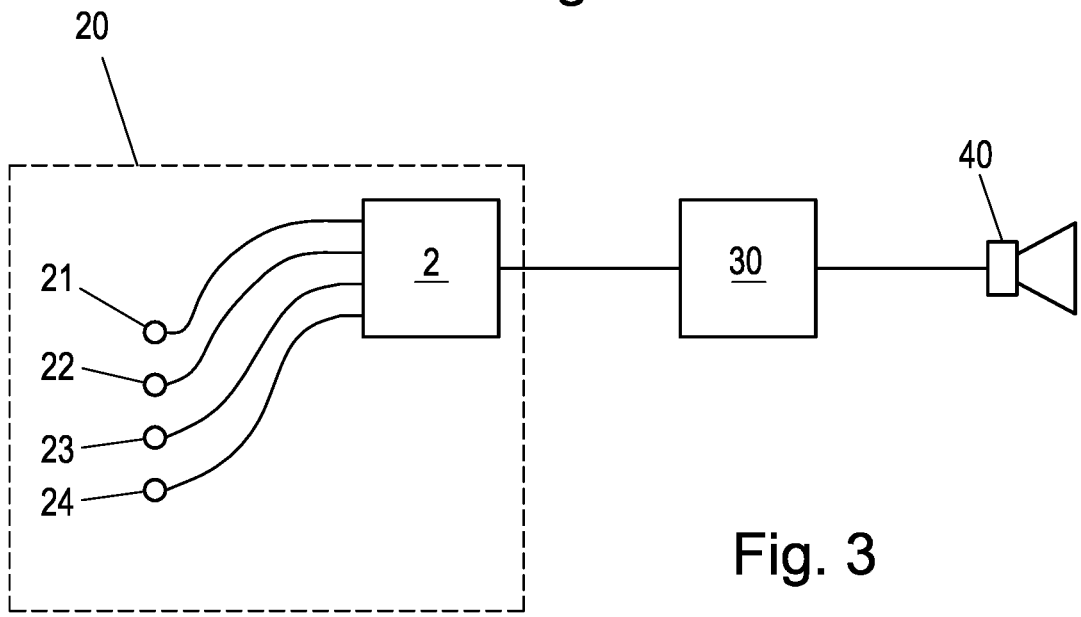
FIG. 3 schematically shows an arrangement for measuring and further processing of EEG data.

FIG. 1 depicts a subject 1 lying on a bed. A multiplicity of EEG electrodes 21-24, which are all connected to an EEG processing appliance 2, are situated on the head of the subject. Said EEG processing appliance evaluates the individual brain waves emitted by the subject 1 and creates EEG data $U_1$, $U_2$, $U_3$, $U_4$ from these brain waves. Here, different pre-processing and filtering methods may be applied. Ultimately, EEG data $U_1$, $U_2$, $U_3$, $U_4$ are available as a sequence of measured voltage signals, with each of the voltage signals specifying respectively one voltage value for a multiplicity of points in time (FIG. 2). The arrangement comprising the individual EEG electrodes 21-24 and the EEG measuring unit 2 constitutes a brain-computer interface 20. This brain-computer interface 20 is connected to a test and control unit 30 (FIG. 3), which actuates a loudspeaker 40 in the present exemplary embodiment of the invention. By way of example, this loudspeaker 40 may be a loudspeaker 40 arranged in a headset placed onto the subject 1.

In the present exemplary embodiment, the individual stimuli $S_A$, $S_B$ have prescribed intervals between one another and between them and the respective start time of the block $B_1$, $B_2$, $B_3$, $B_4$. Particularly advantageously, the time interval between every stimulus $S_A$, $S_B$ and the respective subsequent stimulus $S_A$, $S_B$ is the same such that the subject 1 is unable to identify when a block $B_1$, $B_2$, $B_3$, $B_4$ ends and the subsequent block $B_1$, $B_2$, $B_3$, $B_4$ starts.

Advantageously, the subject 1 may also be instructed to carry out a specific mental act when a specific stimulus is present, in particular the subject may be instructed to count or calculate, to think of specific movements of body parts, in particular to think of the movement of the extremities. Such thoughts of the subject 1 may be recorded by means of the brain-computer interface 20 and analyzed in the test and control unit 30.

Figure 4:
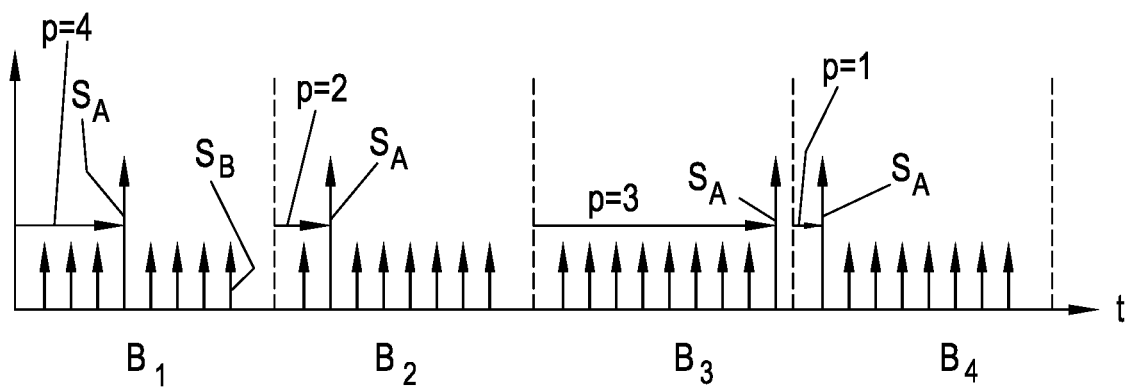
FIG. 4 shows the temporal sequence of the stimuli applied to the subject.

In the present exemplary embodiment, a multiplicity of temporally successive stimuli $S_A$, $S_B$ are applied to the subject 1 (FIG. 4). The stimuli $S_A$, $S_B$ applied to the subject 1 are combined to form blocks $B_1$, $B_2$, $B_3$, $B_4$. Here, each of the blocks $B_1$, $B_2$, $B_3$, $B_4$ comprises a specific number, set to eight in the present case, of stimuli $S_A$, $S_B$ successively applied to the subject 1 and, in this case, respectively one stimulus $S_A$ of the first type is situated in each of the blocks $B_1$, $B_2$, $B_3$, $B_4$ at a specific position with regard to the respective block $B_1$, $B_2$, $B_3$, $B_4$. Stimuli $S_B$ of a second type of blocks are situated at the other positions.

Figure 5:
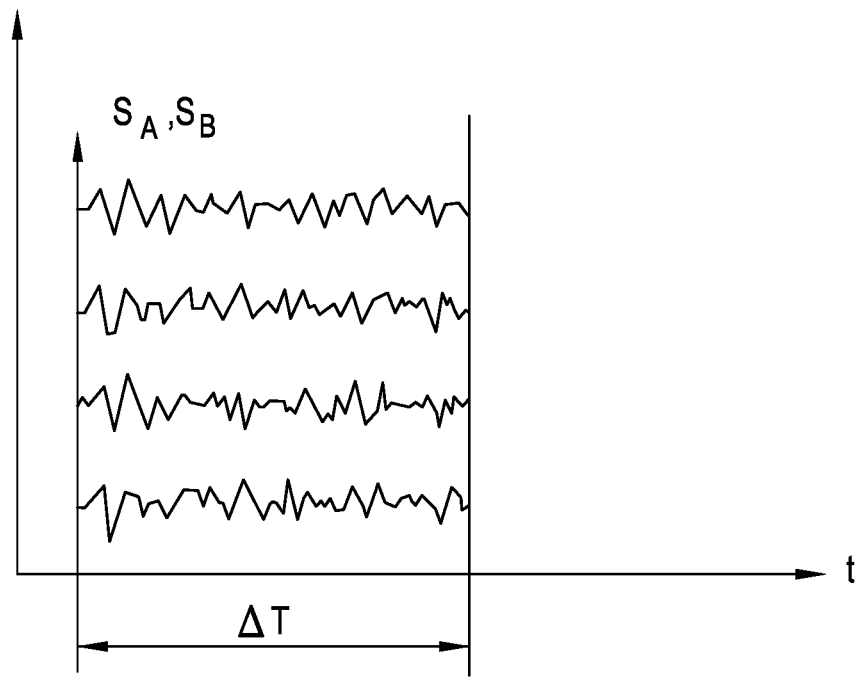
FIG. 5 shows the EEG data assigned to a stimulus.

In the present exemplary embodiment, the stimuli $S_A$ of the first type are high sounds played for the subject 1 while the stimuli $S_B$ of the second type are lower sounds played for the subject 1. In the present exemplary embodiment, each block $B_1$, $B_2$, $B_3$, $B_4$ comprises one high sound $S_A$ and seven low sounds $S_B$ in each case. The procedure depicted in FIG. 5 is carried out in more detail for each individual sound: the reaction of the subject 1 in the form of EEG data $U_1$, $U_2$, $U_3$, $U_4$ is determined after each of the stimuli $S_A$, $S_B$ by virtue of the EEG data $U_1$, $U_2$, $U_3$, $U_4$ of the subject 1 which are caused by the respective stimulus $S_B$ or which are in a temporal relationship therewith being ascertained. These EEG data $U_1$, $U_2$, $U_3$, $U_4$ are assigned to the respective stimulus $S_A$, $S_B$ and the respective block $B_1$, $B_2$, $B_3$, $B_4$ at the relevant position. In the present exemplary embodiment, the EEG data $U_1$, $U_2$, $U_3$, $U_4$ recorded after the stimulus $S_A$, $S_B$ within a timeframe of −100 to +700 ms are respectively used for each of the stimuli $S_A$, $S_B$ and assigned to the respective stimulus $S_A$, $S_B$. Optionally, it is also possible to use EEG data $U_1$, $U_2$, $U_3$, $U_4$ which were recorded within a certain timeframe before the stimulus $S_A$, $S_B$ was emitted.

Figure 6:
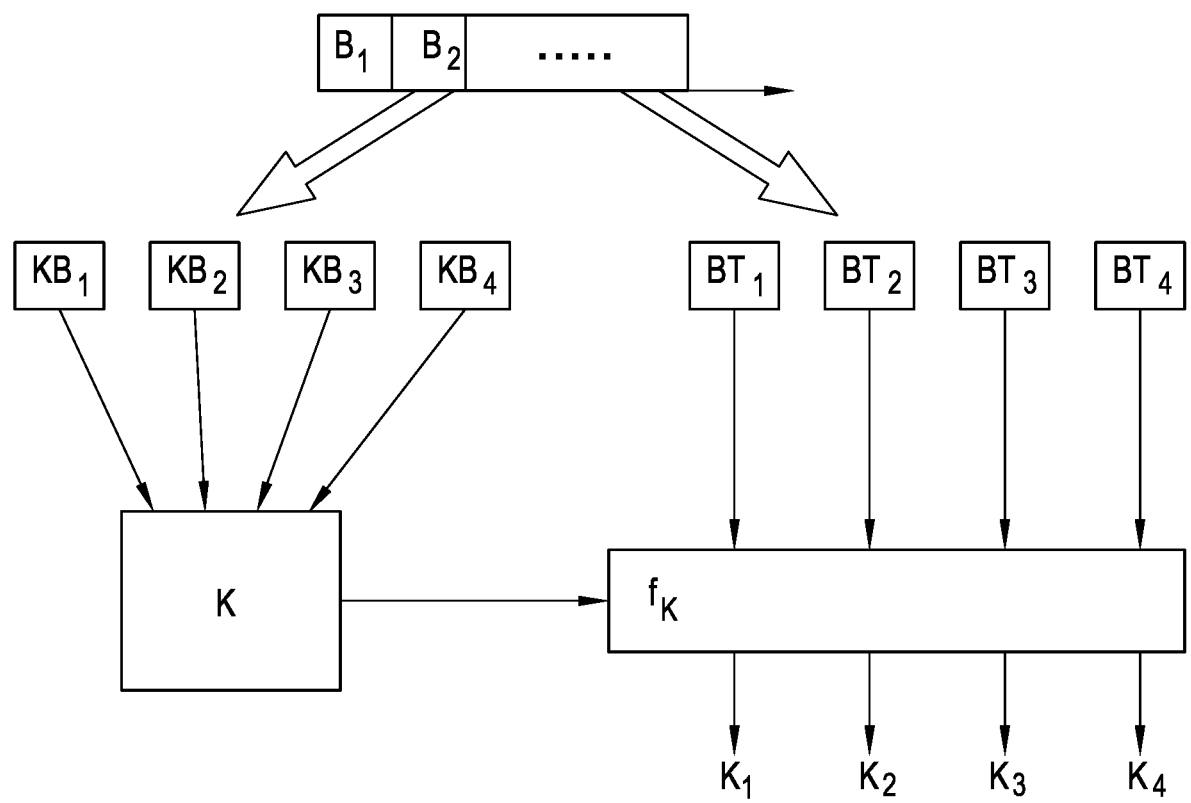
FIG. 6 schematically shows the procedure in an embodiment of a method according to the invention.

Calibration data are created from the totality of the EEG data $U_1$, $U_2$, $U_3$, $U_4$ obtained thus with the respectively assigned stimulus $S_A$, $S_B$ by virtue of the EEG data $U_1$, $U_2$, $U_3$, $U_4$ assigned to a stimulus being combined together with the respective stimulus $S_A$, $S_B$ to form calibration blocks $KB_1$, $KB_2$, $KB_3$, $KB_4$ (FIG. 6). In accordance with the blocks, the individual calibration blocks $KB_1$, $KB_2$, $KB_3$, $KB_4$ are respectively combined in such a way that the EEG data $U_1$, $U_2$, $U_3$, $U_4$ of the subject 1 when a first stimulus $S_A$ is applied are respectively assigned to one position in each case, while EEG data $U_1$, $U_2$, $U_3$, $U_4$ of the subject 1 when applying a further stimulus $S_B$ are assigned to the remaining positions. Incidentally, the calibration blocks $KB_1$, $KB_2$, $KB_3$, $KB_4$ may be combined in random fashion, and so, in particular, it is not necessary for the totality of individual blocks $B_1$, $B_2$, $B_3$, $B_4$ applied to the subject 1 to be selected as calibration blocks $KB_1$, $KB_2$, $KB_3$, $KB_4$. The calibration blocks $KB_1$, $KB_2$, $KB_3$, $KB_4$ may also be created in such a way that EEG data $U_1$, $U_2$, $U_3$, $U_4$ and individual stimuli are selected according to random criteria and once again combined to form calibration blocks $KB_1$, $KB_2$, $KB_3$, $KB_4$, wherein the positions p of the stimuli $S_A$, $S_B$ and EEG data $U_1$, $U_2$, $U_3$, $U_4$ may be varied.

By way of example, 80% of the available EEG data $U_1$, $U_2$, $U_3$, $U_4$ or 80% of the available recorded blocks $B_1$, $B_2$, $B_3$, $B_4$ may be used for creating the calibration blocks $KB_1$, $KB_2$, $KB_3$, $KB_4$. In a further step, the individual EEG data $U_1$, $U_2$, $U_3$, $U_4$ are subjected to a classification analysis K, wherein a classification function $f_K$ is ascertained on the basis of the ascertained calibration blocks $KB_1$, $KB_2$, $KB_3$, $KB_4$, said classification function specifying the position p of the stimulus $S_A$ of the first type in the respective block or calibration block on the basis of EEG data $U_1$, $U_2$, $U_3$, $U_4$ of a block $B_1$, $B_2$, $B_3$, $B_4$ or calibration block $KB_1$, $KB_2$, $KB_3$, $KB_4$ of EEG data $U_1$, $U_2$, $U_3$, $U_4$.

Here, it is advantageously possible for the classification analysis in respect of the calibration blocks $KB_1$, $KB_2$, $KB_3$, $KB_4$ to be carried out using one of the classification methods presented below:
- discriminant function analysis, in particular linear discriminant function analysis,
- support vector machines,
- neural networks.

In all of the methods specified above, it is possible, proceeding from the EEG data $U_1$, $U_2$, $U_3$, $U_4$ ascertained when recording a block $B_1$, $B_2$, $B_3$, $B_4$, to make a statement in respect of the position p of the stimulus $S_A$ of the first type within the respective block $B_1$, $B_2$, $B_3$, $B_4$.

The remaining ascertained blocks $BT_1$, $BT_2$, $BT_3$, $BT_4$, in particular at least 10% of the remaining blocks $BT_1$, $BT_2$, $BT_3$, $BT_4$, or the remaining EEG data $U_1$, $U_2$, $U_3$, $U_4$ are subjected to the ascertained classification function $f_K$ as test blocks. A classification result K is ascertained, said classification result specifying whether the position p at which the stimulus $S_A$ of the first type is situated in the respective test block $BT_1$, $BT_2$, $BT_3$, $BT_4$ corresponds to the classification result K. The number n of test blocks $BT_1$, $BT_2$, $BT_3$, $BT_4$ for which a correspondence is identified is used as a measure M of the perception or perceptive quality of a subject 1 at the time of recording the EEG data $U_1$, $U_2$, $U_3$, $U_4$.

In a preferred embodiment of the invention, it is possible to execute the steps of forming a classification function $f_K$ and of applying the respective classification function $f_K$ to the test blocks $BT_1$, $BT_2$, $BT_3$, $BT_4$ multiple times. Here, a separate measure $M_1, \ldots, M_n$ is ascertained for the perception or perceptive quality of the subject 1 in each case for each individual execution of these steps. A further measure $M^*$ for the perception or perceptive quality may be ascertained from these individual measures $M_1, \ldots, M_n$, for example by averaging or aggregating the individual ascertained separate measures $M_1, \ldots, M_n$.

Figure 7:
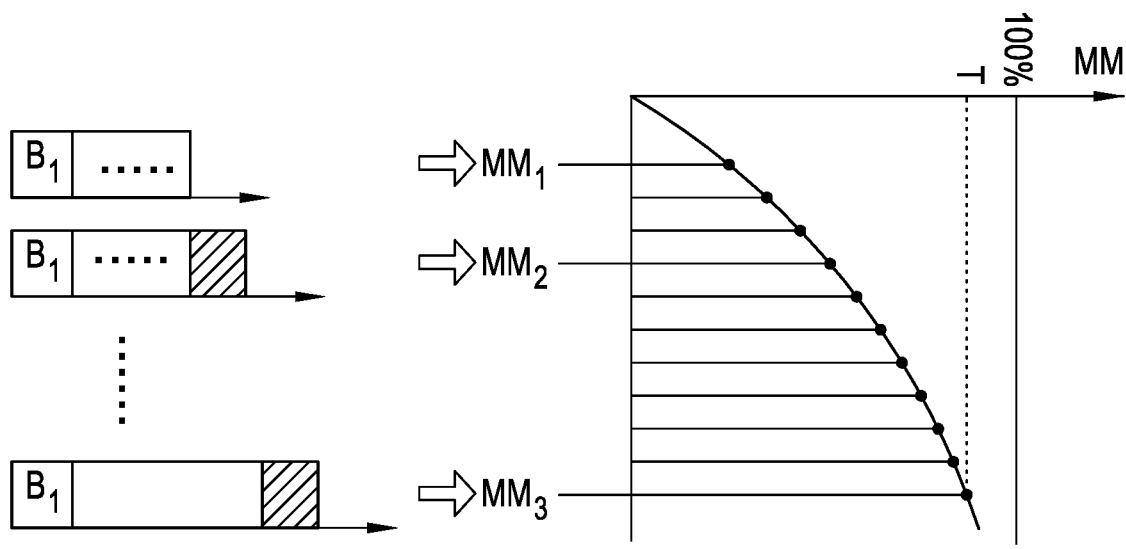
FIG. 7 schematically shows the procedure in a preferred embodiment of a method according to the invention.

A further method in accordance with a preferred embodiment of the invention has the advantage that it can access to a continuously increasing amount of ascertained or recorded blocks $B_1, B_2, B_3, B_4$ (FIG. 7). Here, blocks of EEG data $U_1$, $U_2$, $U_3$, $U_4$ are ascertained continuously, wherein, after recording one or more blocks $B_1, B_2, B_3, B_4$, a calibration function $f_K$ is respectively ascertained separately on the basis of the previously ascertained blocks $B_1, B_2, B_3, B_4$, and the remaining ascertained blocks $B_1, B_2, B_3, B_4$ or some of the remaining ascertained blocks are subjected to the classification function $f_K$. In this case, a separate measure $MM_1, \ldots, MM_n$ for the perception or perceptive quality of the subject 1 is ascertained in each case after recording a continuously increasing number of blocks $B_1, B_2, B_3, B_4$. Subsequently, an examination is carried out as to what number n of blocks needs to be recorded until the measure $MM_1, \ldots, MM_n$ for the perception or perceptive quality exceeds a prescribed threshold T.

The number n of blocks required until the ascertained measure $MM_1, \ldots, MM_n$ exceeds the threshold T may be considered to be a further measure $M^{}$ for the perception or perceptive quality of the subject 1. Further, the mean value or median of the individual ascertained measures may be considered to be a further measure $M^{*}$ for the perception or perceptive quality of the subject 1. Advantageously, the threshold T may be set in such a way that the subject 1 correctly assigns more than 90%, in particular more than 95%, of the blocks $B_1, B_2, B_3, B_4$ or, for this block $B_1, B_2, B_3, B_4$, correctly determines the position of the stimulus $S_A$ of the first type in the respective block.

A preferred embodiment of the invention, which may be combined with all aforementioned embodiment variants of the invention, provides for the test to which the subject 1 was subjected to be executed again after a prescribed time interval. What is particularly advantageous in relation to this procedure is that classification functions $f_K$ are already available for the relevant subject and it is expected that, upon application of the same stimuli $S_A$, $S_B$, the same subject 1 will probably supply the same results, and so there is no need for complicated determination of the classification function $f_K$. This procedure is advantageous, in particular, if little time has passed since determining the classification function $f_K$.

When carrying out the aforementioned tests again, the recorded EEG data $U_1, U_2, U_3, U_4$ and stimuli $S_A$, $S_B$ are once again assigned to one another and combined to form further blocks $B_1', B_2', B_3', B_4'$, wherein these further blocks $B_1', B_2', B_3', B_4'$ have the same design as the calibration blocks $KB_1, KB_2, KB_3, KB_4$ and the blocks $B_1, B_2, B_3, B_4$ ascertained within the scope of the calibration. An individual examination is carried out in each case for each of the further blocks $B_1', B_2', B_3', B_4'$ in respect of whether the position at which the stimulus $S_A$ of the first type is situated in the respective further block $B_1', B_2', B_3', B_4'$ corresponds to the classification result K, i.e. the result of applying the classification function $f_K$ to the further block $B_1', B_2', B_3', B_4'$. The number of further blocks $B_1', B_2', B_3', B_4'$ for which a correspondence was identified is determined and used as a measure $M^*$ for the perception of a subject at the time of recording the further EEG data $U'_1, U'_2, U'_3, U'_4$.

Instead of using sounds with different frequencies, it is also possible, in all aforementioned exemplary embodiments of the invention, to prescribe sounds with different durations or volumes at frequencies that are audible for a human. Alternatively, it is also possible to apply vibrations to different body parts of the relevant subject 1, with intensity and duration of the vibrations differing and a distinction being possible between the first stimulus and further stimuli $S_A$, $S_B$ on account of different intensities or durations of the applications of vibrations.

Alternatively, it is also possible for the set of the types of stimuli $S_A$, $S_B$ to comprise visual stimuli for one eye or both eyes and/or visual stimuli with different intensities and/or durations, which are applied to the subject 1 by means of a screen or by means of a luminous means. Alternatively, the set of the types of stimuli $S_A$, $S_B$ may also comprise electrical stimuli which are exerted on different body parts and/or with different intensities and/or different durations.

Provided that vibrotactile stimuli $S_A$, $S_B$ are applied to the subject 1, it is possible, in a preferred embodiment of the invention after successfully determining perception or a perceptive quality exceeding a threshold, for an application of a functional electrostimulation or an application with an orthosis, a prosthesis or a robot on a region of the body of the subject 1 to exist, by means of which the body of the subject 1 is stimulated at a place or by means of which part of the body of the subject 1, which was stimulated in a vibrotactile manner, is manipulated.

Feedback may be provided to the subject using this measure. Here, the recorded EEG data are classified by means of a previously executed classification analysis. If an ascertained result from the classification is available, an activation stimulus assigned to this result is applied to the subject.

In some cases, it may be advantageous if the above-described procedure is repeated when the subject is exposed to certain influences. Such influences may include:
  cooling or heating of the body or of a part of the body of the subject
  medication
  a change in the oxygen partial pressure in the region of the subject The test is carried out again under these influences. This renders it possible to ascertain the dependence of the perception of the subject 1 depending on the respective external influences.

Here, it is not necessary to form the classification function again in the presence of the external influence. Rather, as described above, the classification function may be maintained. Only the further blocks newly ascertained when the external influence is present are subjected to the classification function. In this manner, a new measure for the perception and perceptive quality is formed and compared to the previously ascertained measure for the perception and perceptive quality.

The invention claimed is:

1. A method of determining a perception or perceptive faculty of a subject by way of a brain-computer interface, the method comprising:
  a) prescribing at least two mutually distinguishable types of stimuli that are configured to instruct the subject to carry out a specific mental act when the stimuli are applied to the subject;
  b) applying to the subject a multiplicity of the stimuli in temporal succession and combining the stimuli to which the subject is subjected into blocks of stimuli, wherein: the blocks of stimuli include the at least two mutually distinguishable types of stimuli applied to the subject temporally in succession, with a stimulus of a first type arranged at a prescribed position of a respective block of stimuli and a stimulus of a second type arranged at a further position of the respective block of stimuli;

c) assessing a reaction of the subject after each of the multiplicity of temporally successive stimuli are applied by recording EEG data of the subject;

d) ascertaining a temporal relationship between each response in the recorded EEG data with the stimuli applied to the subject for each block of stimuli; and e) associating each response in the recorded EEG data with its respective block of stimuli;

f) creating calibration data from the recorded EEG data by combining a plurality of individual responses in the recorded EEG data with their respective blocks of stimuli associated with the individual responses in the recorded EEG data to form calibration blocks, wherein the recorded EEG data of the subject upon the application of the first type of stimulus of the multiplicity of temporally successive stimuli are respectively assigned to one position in a respective calibration block and the recorded EEG data of the subject upon the application of the second type of stimulus of the multiplicity of temporally successive stimuli are assigned to remaining positions in the respective calibration block;

g) determining a classification function by way of a classification analysis based on the created calibration blocks, the classification function specifying the one position of the first type of stimulus in the respective calibration block;

h) selecting a plurality of test blocks from the blocks of stimuli and subjecting the recorded EEG data associated with the test blocks to the classification function and deriving a classification result, and examining whether a position at which the first type of stimulus is situated in the respective test block corresponds to the classification result and using a number of test blocks for which the position of the first type of stimulus in the respective test block corresponds to the classification result or a value derived from the classification result as a measure for the perception or the perceptive faculty of the subject at a time of recording further EEG data; and i) outputting the measure for the perception or the perceptive faculty of the subject at the time of recording the further EEG data.

2. The method according to claim 1, wherein step a) comprises prescribing stimuli selected from the group consisting of acoustic, mechanical, electric and optical stimuli, and instructing the subject to count as the specific mental act.

3. The method according to claim 1, which comprises: executing steps f), q), and h) multiple times on a basis of the blocks of stimuli of step b), wherein: respectively during each individual execution of steps f), q), and h) individual blocks of stimuli of step b) are randomly selected in the creation of the calibration blocks, wherein the selection includes at least 50% of the blocks of stimuli of remaining blocks of stimuli; subjecting the not randomly selected blocks of stimuli to the classification function as the selected test blocks in step and a separate measure for the perception or perceptive faculty is ascertained every time steps f), q), and h) are executed; and ascertaining a further measure for the perception or perceptive faculty by averaging or aggregating the separate measures obtained in individual executions of steps f), q), and h).

4. The method according to claim 1, which comprises: continuously defining the blocks of stimuli in accordance with step b) and respectively executing steps f), q), and h) on a basis of the blocks of step b) after the recorded EEG data of one or more blocks of stimuli were arranged at a relevant position; wherein, respectively during each individual execution of steps f), g), and h), individual blocks of stimuli of step b) are randomly selected in step f) in the creation of the calibration blocks, wherein the selection includes at least 50% of the blocks of stimuli; the not randomly selected blocks of stimuli are subjected to the classification function as the test blocks in step h); a separate measure for the perception or perceptive faculty is respectively ascertained every time f), g), and h) are executed; and carrying out an examination in respect of how many blocks are recorded before the separate measure for the perception or perceptive faculty exceeds a prescribed threshold, and ascertaining a number of blocks as a further measure for the perception or perceptive faculty and/or ascertaining a mean value or a median of the individual separate measures as a further measure for the perception or perceptive faculty.

5. The method according to claim 1, which comprises: randomly selecting at least 50% of the blocks of stimuli in step f) for the creation of the calibration blocks; subjecting at least 10% of the not selected blocks of stimuli, to the classification function as the test blocks in step h) and carrying out an examination as to whether the position at which the stimulus of the first type is situated in the respective test block corresponds to the classification result.

6. The method according to claim 1, which comprises applying a plurality of successive further stimuli to the subject, the further stimuli being combined in accordance with step b) to form further blocks, and carrying out an individual examination in each case for the further blocks as to whether a position at which the first stimulus is situated in the respective further block corresponds to the classification result, and using a number of further blocks for which a correspondence is identified as the measure for the perception or the perceptive faculty of the subject at the time of recording the further EEG data.

7. The method according to claim 1, which comprises: applying at least one of the at least two mutually distinguishable types of stimuli to the subject in the form of a vibrotactile stimulus, and applying a further stimulus being an activation stimulus to the subject if the classification result exceeding a threshold is present.

8. The method according to claim 7, wherein the application of the multiplicity of the stimuli to the subject consists of:
   an application of functional electro stimulation; or
   a vibrotactile application with an orthosis, a prosthesis or a robot on a region of a body of the subject, wherein the body of the subject is stimulated at a given location or a part of the body of the subject.

9. The method according to claim 1, wherein:
   the at least two mutually distinguishable types of stimuli are prescribed by different sounds having different durations, frequencies and volumes, at frequencies that are audible for a human and the respective sound is played to the subject; or
   the at least two mutually distinguishable types of stimuli comprise applications of vibrations by way of vibration units to different body parts and/or with different intensities and/or durations.

10. The method according to claim 1, wherein:
- the at least two mutually distinguishable types of stimuli are visual stimuli for one eye or both eyes that are applied with different intensities and/or durations by way of a display screen or by way of a luminous device; or
- the at least two mutually distinguishable types of stimuli are electrical stimuli applied at different body parts or electrical stimuli with different intensities and/or durations, and the electrical stimuli are applied to the subject by way of electrical stimulators.

11. The method according to claim 1, wherein the mental act that the subject is instructed to carry out is one of the following mental acts:
- counting or calculating;
- thinking of movements of body parts;
- thinking of a movement of an extremity at a right or left body half.

12. The method according to claim 1, wherein the step of carrying out the classification analysis comprises a discriminant function analysis, support vector machines, and neural networks.

13. The method according to claim 1, further comprising, after step h):
- bringing the subject into different states by cooling or heating a body or a part of the body by medication or by changing an oxygen partial pressure in a region of the subject, and
- repeating steps b) through to examine the perception or perceptive faculty according to the same criteria and comparing a new measure for the perception or perceptive faculty determined in the repeated step with the measure of the perception or perceptive faculty determined in the first-executed step h).

14. The method according to claim 1, further comprising, after determining of the classification function in step g):
- bringing the subject into different states by cooling or heating a body or a part of the body by medication and/or by changing an oxygen partial pressure in a region of the subject, and
- applying a number of successive further stimuli to the subject, the further stimuli being combined in accordance with step b) to form further blocks;
- carrying out an individual examination in each case for the further stimuli as to whether a position at which the stimulus of the first type is situated in the respective further block corresponds to the classification result, and
- using a number of further blocks for which a correspondence is identified as a new measure for the perception or the perceptive faculty of the subject at a time of recording the further EEG data; and
- comparing the measure and the new measure to one another.

15. The method according to claim 1, which comprises classifying the recorded EEG data by way of a previously executed classification analysis and, if an ascertained result is available from the classification analysis, applying an activation stimulus assigned to the ascertained result to the subject.

* * * * *